(12) United States Patent
Mulholland et al.

(10) Patent No.: US 7,837,692 B2
(45) Date of Patent: Nov. 23, 2010

(54) CATHETER WITH AN EXPANDABLE END PORTION

(75) Inventors: Patrick Mulholland, Mullingar (IE); Gerard O'Carroll, Castlebaldwin (IE); Dominic Conlon, Geevagh (IE); David Vale, Clontarf (IE); Eamon Brady, Elphin (IE)

(73) Assignee: Salviac Limited, Dublin (IE)

( * ) Notice: Subject to any disclaimer, the term of this patent is extended or adjusted under 35 U.S.C. 154(b) by 120 days.

(21) Appl. No.: 11/480,473

(22) Filed: Jul. 5, 2006

(65) Prior Publication Data

US 2006/0264972 A1    Nov. 23, 2006

Related U.S. Application Data

(63) Continuation of application No. 10/383,254, filed on Mar. 7, 2003, now Pat. No. 7,094,243, which is a continuation of application No. 09/915,135, filed on Jul. 26, 2001, now abandoned, which is a continuation of application No. PCT/IE00/00011, filed on Jan. 28, 2000.

(51) Int. Cl.
*A61B 17/22* (2006.01)
*A61B 17/34* (2006.01)
*A61B 1/32* (2006.01)
*A61M 29/00* (2006.01)
*A61M 25/00* (2006.01)

(52) U.S. Cl. ............... 606/108; 606/127; 606/198; 606/185; 606/200; 604/104; 604/264; 604/523; 604/524; 600/200; 600/201

(58) Field of Classification Search .......... 606/108, 606/127, 198, 185, 200; 604/104, 264, 523, 604/524; 600/200–201
See application file for complete search history.

(56) References Cited

U.S. PATENT DOCUMENTS

| 4,531,943 | A |   | 7/1985  | Van Tassel et al.        |
|-----------|---|---|---------|--------------------------|
| 4,611,594 | A | * | 9/1986  | Grayhack et al. .. 606/127|
| 4,790,812 | A |   | 12/1988 | Hawkins, Jr. et al.      |
| 4,873,978 | A |   | 10/1989 | Ginsburg                 |
| 4,927,426 | A | * | 5/1990  | Dretler ............ 606/2.5|
| 4,938,220 | A |   | 7/1990  | Mueller, Jr.             |
| 5,030,201 | A | * | 7/1991  | Palestrant ........ 604/22|
| 5,092,839 | A |   | 3/1992  | Kipperman                |

(Continued)

FOREIGN PATENT DOCUMENTS

DE    2 945 237    5/1981

(Continued)

*Primary Examiner*—Thomas C Barrett
*Assistant Examiner*—Sameh Boles
(74) *Attorney, Agent, or Firm*—Sughrue Mion, PLLC; Jonathan Feuchtwang

(57) ABSTRACT

A catheter (2) is used in medical applications, for example for the retrieval of a sample from a patient or the insertion or retrieval of medical devices such as filters, stents (3) to and from the patient. The catheter (2) includes an expandable tip (6) at a leading portion of a catheter tube portion (5). This expandable tip (6) can retrieve or deliver samples, medical devices, etc. (3), which are slightly larger than the dimensions of a main catheter tube (5) inserted into the patient. The expandable tip (6) can also include extension members (10) which provide axial support to the expandable tip (6) but which still allow expansion in the radial direction.

18 Claims, 4 Drawing Sheets

U.S. PATENT DOCUMENTS

| | | | |
|---|---|---|---|
| 5,102,415 A | 4/1992 | Guenther et al. | |
| 5,108,406 A | 4/1992 | Lee | |
| 5,171,233 A | 12/1992 | Amplatz et al. | |
| 5,203,773 A | 4/1993 | Green | |
| 5,234,425 A | 8/1993 | Fogarty et al. | |
| 5,234,437 A | 8/1993 | Sepetka | |
| 5,256,150 A | 10/1993 | Quiachon et al. | |
| 5,266,669 A | 11/1993 | Onwunaka et al. | |
| 5,312,417 A | 5/1994 | Wilk | |
| 5,330,444 A | 7/1994 | Webler et al. | |
| 5,397,320 A * | 3/1995 | Essig et al. | 606/37 |
| 5,423,851 A | 6/1995 | Samuels | |
| 5,447,503 A * | 9/1995 | Miller | 604/528 |
| 5,509,900 A * | 4/1996 | Kirkman | 604/104 |
| 5,549,626 A | 8/1996 | Miller et al. | |
| 5,676,423 A * | 10/1997 | Pedronno et al. | 297/378.1 |
| 5,676,681 A * | 10/1997 | Yoon | 606/185 |
| 5,685,320 A | 11/1997 | Zimmon et al. | |
| 5,707,359 A | 1/1998 | Bufalini | |
| 5,725,550 A * | 3/1998 | Nadal | 606/200 |
| 5,868,753 A | 2/1999 | Schatz | |
| 5,908,435 A | 6/1999 | Samuels | |
| 5,924,175 A * | 7/1999 | Lippitt et al. | 24/537 |
| 6,015,423 A * | 1/2000 | Andrese | 606/198 |
| 6,080,141 A * | 6/2000 | Castro et al. | 604/523 |
| 6,130,406 A | 10/2000 | Cheer | |
| 6,156,055 A * | 12/2000 | Ravenscroft | 606/206 |
| 6,187,016 B1 * | 2/2001 | Hedges et al. | 606/108 |
| 6,187,017 B1 | 2/2001 | Gregory, Jr. | |
| 6,196,966 B1 * | 3/2001 | Kerin et al. | 600/114 |
| 6,280,464 B1 * | 8/2001 | Hayashi | 623/1.11 |
| 6,350,271 B1 | 2/2002 | Kurz et al. | |
| 6,383,195 B1 | 5/2002 | Richard | |
| 6,440,120 B1 | 8/2002 | Maahs | |
| 6,508,966 B1 | 1/2003 | Castro et al. | |
| 6,599,304 B1 * | 7/2003 | Selmon et al. | 606/159 |
| 2002/0058963 A1 | 5/2002 | Vale et al. | |
| 2002/0107479 A1 | 8/2002 | Bates et al. | |
| 2002/0133127 A1 | 9/2002 | Collins | |
| 2003/0181922 A1 | 9/2003 | Alferness | |

FOREIGN PATENT DOCUMENTS

| | | |
|---|---|---|
| EP | 0 200 668 | 11/1986 |
| EP | 0 743 046 A1 | 11/1996 |
| FR | 2 677 872 | 12/1992 |
| JP | P2003-190292 | 7/2003 |
| WO | WO 98/08562 | 3/1998 |
| WO | WO 99/23957 | 5/1999 |
| WO | 01/12082 A1 | 2/2001 |

* cited by examiner

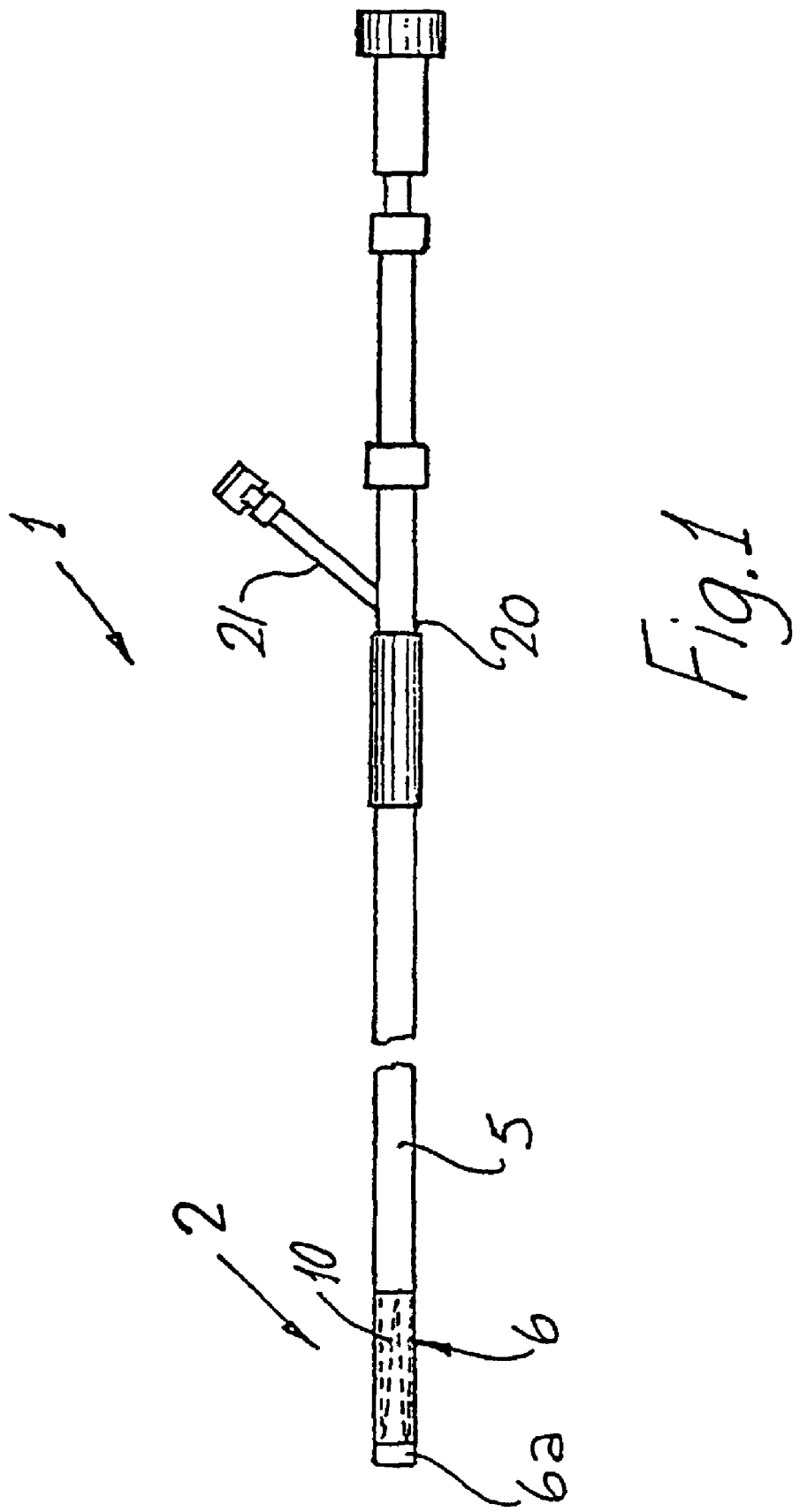

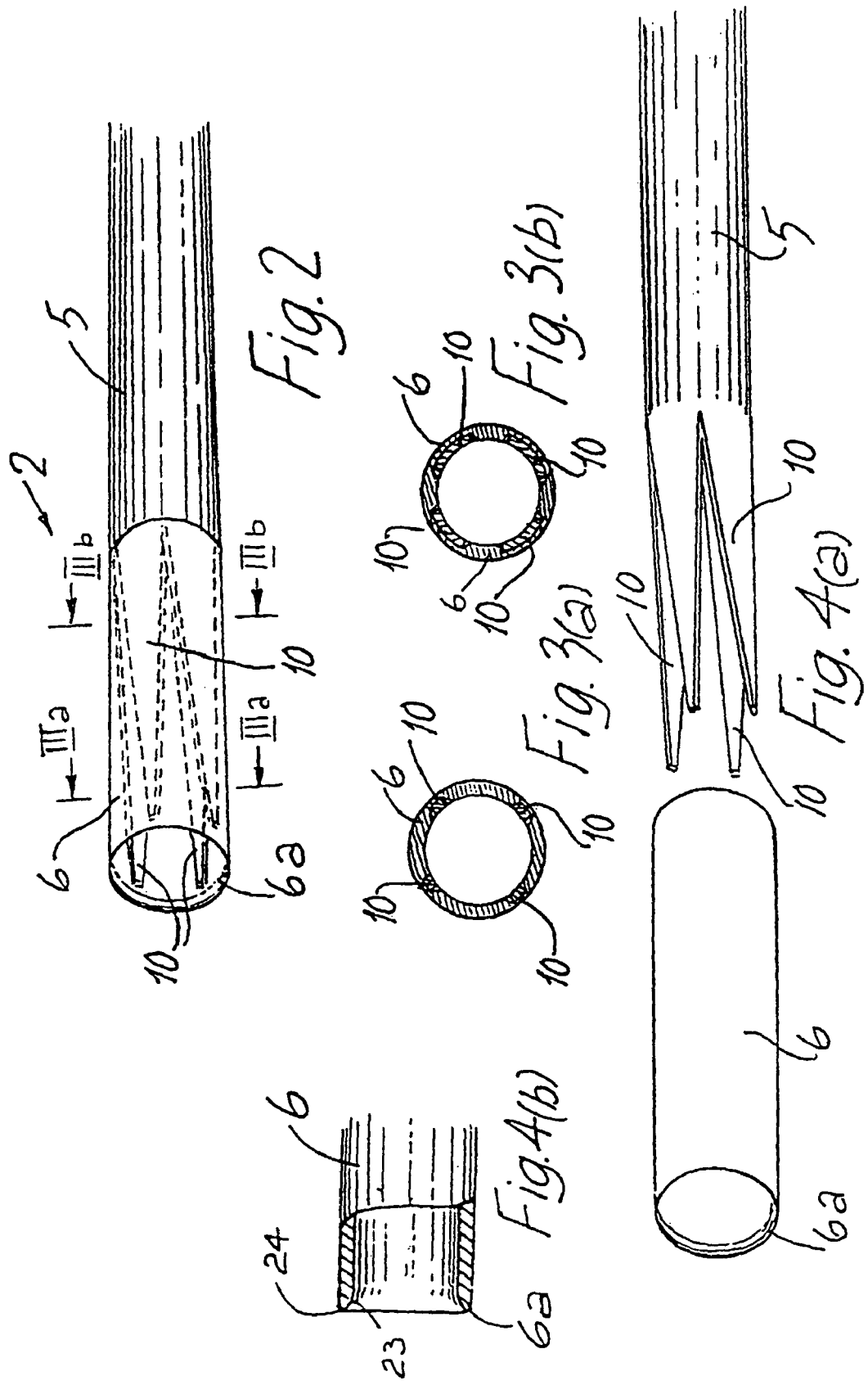

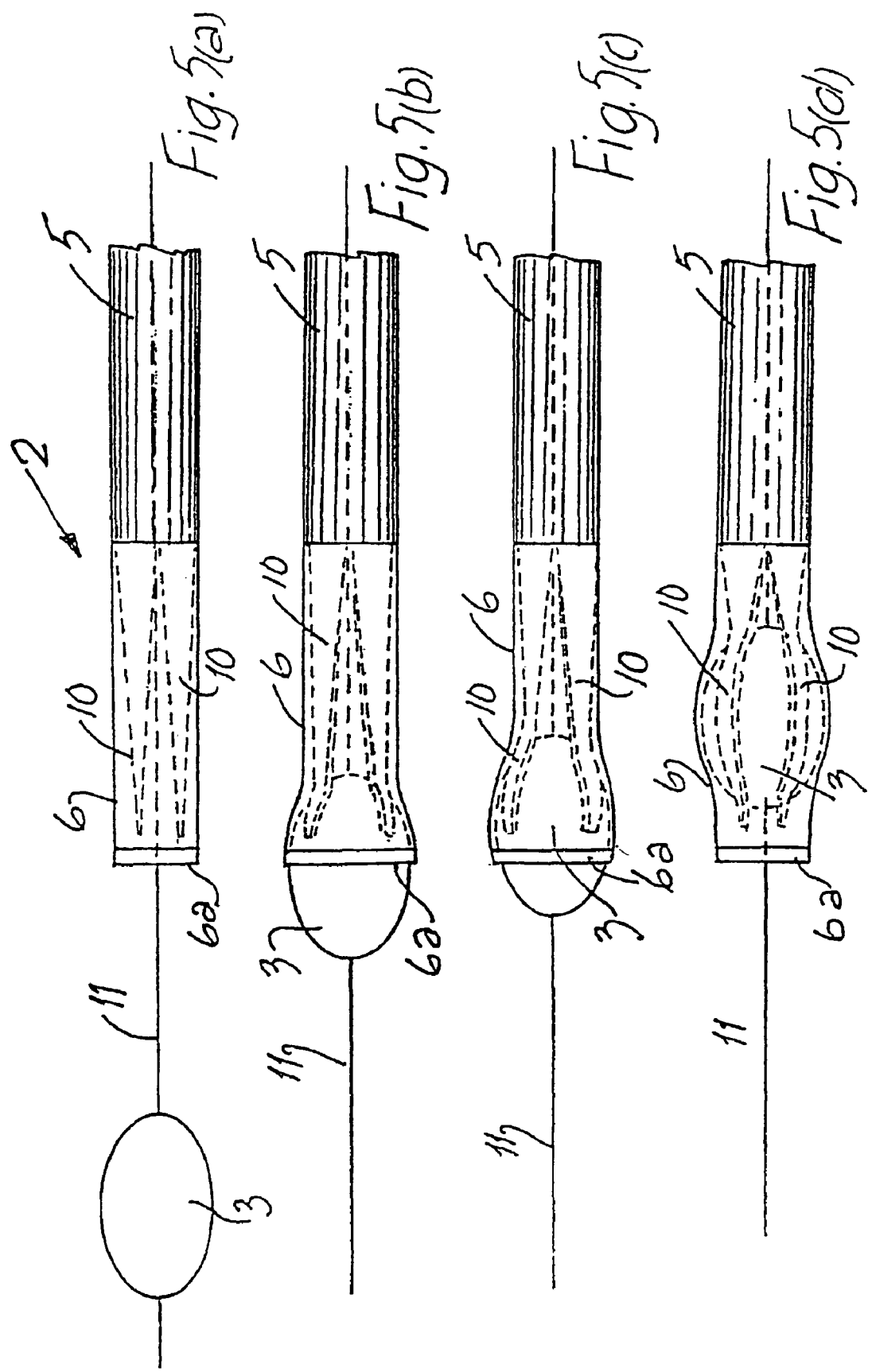

CATHETER WITH AN EXPANDABLE END PORTION

This is a continuation of application Ser. No. 10/383,254 filed Mar. 7, 2003, now U.S. Pat. No. 7,094,243, which is a Continuation Application of U.S. application Ser. No. 09/915,135 filed Jul. 26, 2001, now abandoned, which in turn is a Continuation of PCT Application No. PCT/IE00/00011 filed Jan. 28, 2000. The entire disclosures of the prior applications, application Ser. Nos. 09/915,135 and 10/383,254 are considered part of the disclosure of the accompanying continuation application and are hereby incorporated by reference.

BACKGROUND OF THE INVENTION

1. Field of the Invention

The present invention is directed to a catheter, for example a retrieval or delivery catheter used in medical applications, which has an expandable end portion.

2. Discussion of the Background

Catheters are well known medical devices used to facilitate various medical procedures, such as diagnostic or delivery procedures. Catheter tubes are inserted into a body of a patient for various medical procedures. For example, a catheter may be used in performing diagnostic procedures such as removing a sample from a body site of a patient. The catheter tube is used in this situation as the delivery vehicle for the medical instrument which removes the sample. Further, sophisticated medical implant devices, such as filters and stents, can be delivered and retrieved into and from the body site of the patient using a catheter.

Generally, a catheter has a tube portion which is relatively stiff in both axial and radial directions to allow proper placement of the catheter in the patient's body, but which may be fitted with a distal soft tip which first contacts tissues in the patient. The soft tip is provided to minimise discomfort for the patient when the catheter is inserted into the patient. For example, WO-A-9808562 A describes a catheter with an insert moulded catheter tip. However, there are constraints on the use of such catheters in that such catheters can only be relatively small sized, and thus can only be used to retrieve and deliver relatively small samples and medical devices.

SUMMARY OF THE INVENTION

Accordingly, one object of the present invention is to provide a novel catheter which can be used to retrieve larger objects and deliver and retrieve larger medical devices than in the background art.

A further object of the present invention is to provide a novel catheter which can accommodate an article with a slightly larger dimension than that of a main catheter tube itself.

The novel catheter of the present invention achieves these and other objects by including a portion near a distal tip end which is expandable in size in a radial direction to accommodate larger size samples or medical devices. The catheter includes reinforcement means to enhance the axial strength of the tip while facilitating radial expansion of the tip to accommodate an article.

As a further feature, the novel catheter of the present invention can further include reinforcing portions in the expandable portion to enhance strength in the axial direction, while still allowing expansion in the radial direction.

Most preferably the tip is a soft tip of flexible material.

In a preferred embodiment the reinforcement means comprises an extension means extending from the catheter tube portion. Preferably the tip includes a free distal end and the extension means terminates at a position that is axially spaced back from the free end of the tip.

In one embodiment of the invention the extension means comprises at least one extension member extending from said catheter tube portion into said expandable tip.

Preferably the extension means comprises a plurality of extension members extending from said catheter tube portion into said expandable tip. To provide a gradual change in the axial reinforcement preferably said at least one extension member is tapered toward a leading portion of said expandable tip.

Axial reinforcement and radial expansion is facilitated particularly when said plurality of extension members are equispaced in the direction of said expandable member.

Preferably said plurality of extension members are tapered toward a leading portion of said expandable member.

For ease of manufacture while providing the desired reinforcement characteristics preferably the number of said plurality of extension members is four.

To provide atraumatic transition to the soft tip preferably said at least one extension member includes a radiused tip. Ideally, said plurality of extension members each include a radiused tip.

In addition, for ease of passage of an article into or out of the tip preferably the tip has a free end which is rounded.

In a preferred embodiment the tip has a free end which is rounded for ease of passage of the tip through a body passageway such as the vasculature.

Preferably the tip comprises a tubular sleeve of flexible material. For ease of manufacture and to provide a smooth transition preferably the sleeve is attached to the catheter tube portion by heating.

Ideally to provide a smooth transition the tip has an outer diameter which is approximately the same dimension as the outer diameter of the catheter tube portion.

In one aspect the invention provides a retrieval catheter for retrieving an article such as a filter comprising a catheter tube portion and a tip extending axially from the catheter tube portion, the tip being flexible relative to the catheter tube portion, characterised in that the catheter includes reinforcement means to enhance the axial strength of the tip while facilitating radial expansion of the tip to accommodate an article in the tip. Usually the article to be retrieved has a larger dimension then that of the normal internal dimension of the tip.

In one embodiment of the invention the tip is movable from a delivery configuration in which the outer diameter of the tip is approximately of the same dimension as the outer diameter of the catheter portion to which it is attached, to an expandable position as an article is received in the tip.

For ease of use, preferably the tip is progressively movable to the expanded position in response to receiving an article in the tip.

The invention also provides a catheter tube portion having a tip extending axially from the catheter tube portion, in which the catheter tube portion includes reinforcement means to enhance the axial strength of the tip while facilitating radial expansion of the tip to accommodate an article in the tip.

BRIEF DESCRIPTION OF THE DRAWINGS

The invention will be more clearly understood by reference to the following detailed description when considered in conjunction with the accompanying drawings, wherein:

FIG. 1 is an overall view of the novel catheter of the present invention used with an introducer;

FIG. 2 shows a more detailed view of a tip portion of the catheter of FIG. 1;

FIGS. 3(a) and 3(b) are cross sectional views of the tip portion of the catheter on the lines IIIa-IIIa and IIIb-IIIb respectively of FIG. 2;

FIG. 4(a) is an exploded view of the tip portion of the catheter of the present invention;

FIG. 4(b) is a cross sectional view on an enlarged scale of a distal end of the tip portion of the catheter;

FIGS. 5(a) to 5(d) are diagrammatic views showing one operation of the catheter.

DESCRIPTION OF THE PREFERRED EMBODIMENTS

Figure 6:
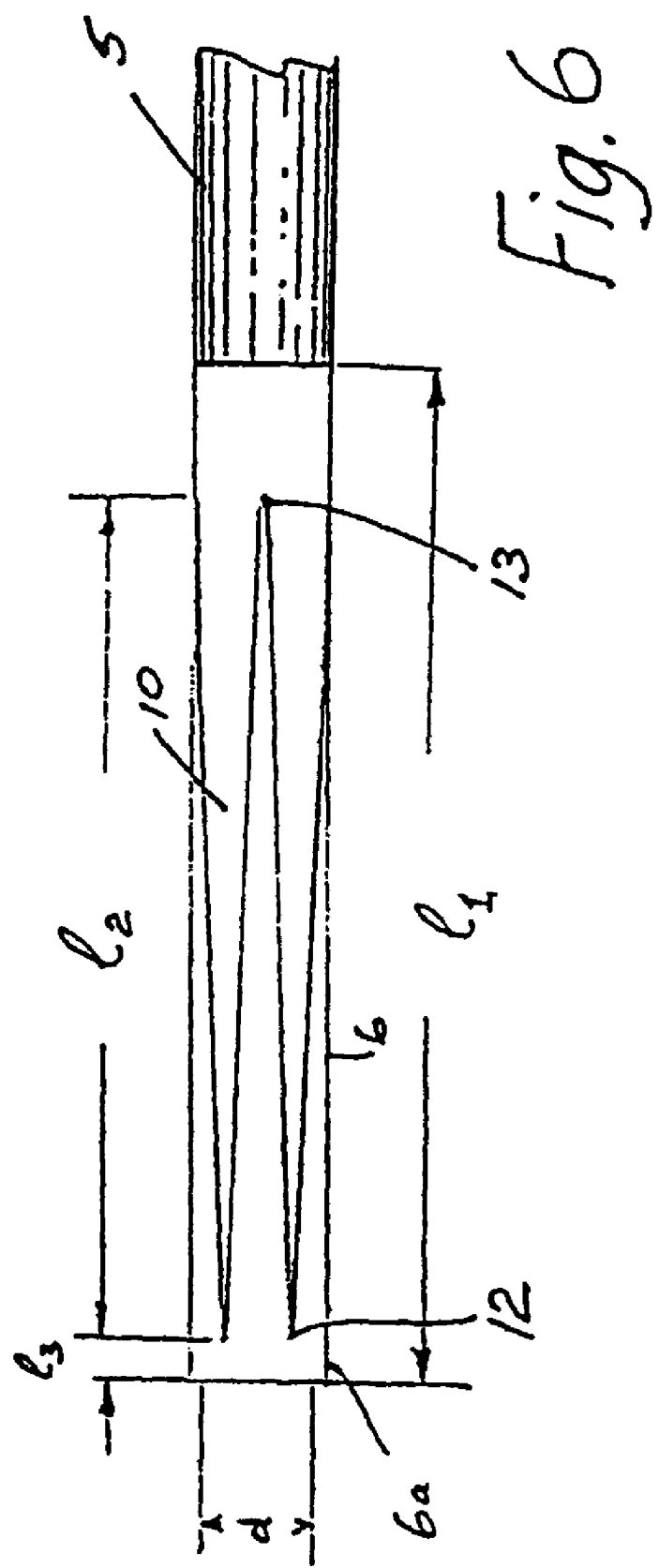
FIG. 6 is a scale drawing, as an example, of an actual implementation of the novel catheter of the present invention.

Referring to the drawings, wherein like reference numerals designate identical or corresponding parts throughout the several views, and more particularly to FIG. 1 thereof, the overall device 1 is an introducer, e.g. a percutaneous introducer, with a catheter portion 2. FIG. 1 illustrates the catheter portion 2 according to the present invention, for example a retrieval catheter, which is attached to an introducer having a hub portion 20 and a side lead tube 21 which leads into the hub portion 20. A medical instrument to be inserted into a patient is placed through the hub portion 20. This medical instrument placed through the hub portion 20 may be, as examples, a retrieval element to retrieve a sample, a clot or previously inserted medical device such as a stent or filter from a patient's body, or a delivery element to deliver a medical device to a patient's body.

The catheter 2 may also be used to deliver or retrieve another catheter. The catheter portion 2 of FIG. 1 includes a catheter tube portion 5 which is relatively rigid in both the axial and radial directions to facilitate delivery of the catheter tube portion 5 through a lumen. That is, the catheter tube portion 5 is a portion actually inserted into the patient.

The catheter portion 2 of the present invention further includes an expandable soft tip portion 6 with a distal tip area 6a. The expandable tip 6 is in the form of a sleeve which has an outer diameter which is nominally the same as the outer diameter of the catheter tube portion 5. The distal soft tip area 6a initially contacts tissues of the patient as the catheter tube portion 5 is inserted into the patient, and minimises discomfort in the patient by virtue of its softness. The expandable soft tip portion 6 is flexible in both the axial and radial directions, and particularly is expandable in the radial direction. This expandable tip portion 6 may be made of a radiopaque or non-radiopaque material. Examples of materials for the expandable tip portion 6 include PEBA (polyether block polyamide), nylon, polyurethane or polyethylene.

FIGS. 2, 3 and 4 provide further details of the catheter portion 2 including the expandable soft portion 6. The catheter portion 2 includes extension legs 10 formed inside of the expandable portion 6. That is, the catheter tube portion 5 is processed to form extension legs 10 at the leading edge of the catheter tube portion 5. The extension legs 10 can be formed in the catheter tube portion 5 by, for example, cutting catheter tube portion 5 using a punch and die set with a profile to achieve a desired taper in the extension legs 10. The extension legs 10 provide a reinforcement in the axial direction of the expandable portion 6 over their length to enhance the strength of expandable portion 6 in the axial direction, while still providing expansion in the radial direction. In the embodiment shown in FIGS. 2-4 four extension legs 10 are equispaced around the expandable portion 6 to provide support in the axial direction and uniform flexibility in the radial direction. These extension legs 10 are tapered towards the free end of the expandable portion 6 to provide a gradually increasing controlled axial flexibility to allow the catheter tube portion 5 to be comfortably guided into the patient.

The expandable portion 6, which as noted above can be formed of a radiopaque or non-radiopaque material such as PEBA, nylon, polyurethane or polyethylene, can be secured to the main catheter tube portion 5 by heating such as by RF (radio frequency) welding the expandable portion 6 to the main catheter tube portion 5. On heating, the extension legs 10 merge into the expandable portion 6.

It will be noted that the expandable soft portion 6 extends distally beyond the axial extent of the extension legs 10 to provide the distal soft tip 6a which is not axially reinforced. The soft tip 6a has a free end that is rounded internally at 23 for ease of passage of an article 3, and is also rounded externally at 24 for ease of atraumatic passage of the tip through a body passageway such as the vasculature.

FIG. 6 shows an actual implementation of the catheter portion 2 in the present invention. Element 12 shows distal tips of the extension legs 10, and element 13 shows proximal tips of the extension legs 10, which tips 12, 13 can be radiused. That is, the tips 12, 13 of the extension legs 10 can be rounded to prevent creating a sharp edge, and thereby generating a weak point in the soft tip area 6a or the expandable portion 6. Generating a weak point in the expandable portion 6 could result in a tear in the soft tip, and if the tips 12, 13 of the extension legs 10 are radiused such a weak point and resulting tear may be prevented. Typical dimensions in millimetres are as follows:

| | |
|---|---|
| $l_1$ | 18.00 ± 1.50 |
| $l_2$ | 15.00 ± 0.25 |
| $l_3$ | 0.70 |
| Internal d | 2.03 ± 0.04 |
| Tip radius | R 0.15 @ 90° intervals |

FIGS. 5(a) to 5(d) show the catheter 2 of the present invention in use as a retrieval catheter as an example of one use of catheter 2. As shown in FIG. 5(a), an article 3 for retrieval, for example a sample or clot within a patient or a medical device such as a stent or filter previously inserted in the patient, is approached by the catheter tube portion 5. A retrieval device may be inserted in the introducer 1 and through the hub 20, through the catheter tube portion 5, and then through the expandable portion 6, to contact the sample 3. Alternatively the article 3, especially when in the form of a medical device such as a filter, may be attached, on introduction, to a guide wire 11 as shown in FIG. 5(a). The retrieval device then retrieves the article 3 into the expandable portion 6 of the catheter portion 2 as shown in FIGS. 5(b) to 5(d). The article 3 is first pulled back by pulling the guide wire and engages the distal tip 6a which is not reinforced and expands radially to receive the proximal end of the article 3. As the article 3 is drawn further back into the expandable portion 6 the expandable portion 6 expands radially outwardly. However the expandable portion 6 is gradually axially reinforced by the extension legs 10 to smooth the capture of the article 3. This expandable portion 6 extending axially from the catheter tube portion 5 is flexible relative to the catheter tube portion 5. The catheter portion includes reinforcement means to enhance the axial strength of the expandable portion 6 while facilitating radial expansion of the tip to accommodate an article 3 in the expandable portion 6. The tip expands to accommodate the article 3. As noted above, the extension legs 10 provide some support in the axial direction, but still allow expansion in the radial direction, to thereby allow expandable portion 6 to expand to allow the article 3 to be drawn into the expandable portion 6. The catheter tube portion 5 can then be removed from the patient with the article 3 housed therein.

In this way, this operation in the present invention allows a sample or device 3 which may be larger than the catheter tube portion 5 to be retrieved from a patient. A medical device which may be larger than the catheter tube portion 5 can also be delivered to a patient in a similar manner.

Obviously, numerous modifications and variations of the present invention are possible in light of the above teachings. It is therefore to be understood that within the scope of the appended claims the present invention may be practised otherwise than as specifically disclosed therein.

The invention claimed is:

1. A catheter comprising a catheter tube portion having a proximal end portion and a distal end portion, wherein the distal end portion includes a tip, the tip comprising axial reinforcement legs formed of the catheter tube portion and a soft portion formed of a polymeric material, wherein the soft portion is disposed around the axial reinforcement legs and the tip is more flexible relative to the catheter tube portion, wherein the tip is movable from a delivery configuration in which an outer diameter of the tip is approximately of the same dimension as an outer diameter of the catheter portion to which it is attached, to an expandable position as an article is received in the tip, and wherein, in the delivery configuration, the outer diameter of the tip is constant along the entire length of the tip.

2. A catheter as claimed in claim 1 wherein the tip is radially expansible relative to the catheter tube portion.

3. A catheter as claimed in claim 1 wherein said axial reinforcement legs are equi-spaced in the radial direction around the tip.

4. A catheter as claimed in claim 1 wherein said axial reinforcement legs are tapered toward a leading portion of said tip.

5. A catheter as claimed in claim 1 wherein the number of said axial reinforcement legs is four.

6. A catheter as claimed in claim 1 wherein said axial reinforcement legs include a radiused tip.

7. A catheter as claimed in claim 1 wherein the tip has a free end which is rounded internally for ease of passage of an article.

8. A catheter as claimed in claim 1 wherein the tip has a free end which is rounded externally for ease of passage of the tip through the vasculature.

9. A catheter as claimed in claim 1 wherein the soft portion is attached to the axial reinforcement legs by heating.

10. A catheter as claimed in claim 1 wherein the tip has an outer diameter which is approximately the same dimension as an outer diameter of the catheter tube portion.

11. A catheter as claimed in claim 1 wherein the tip is progressively movable to an expanded position in response to receiving an article in the tip.

12. A catheter as claimed in claim 1 wherein the soft portion is attached to the axial reinforcement legs by RF (radio frequency) welding.

13. A catheter as claimed in claim 1 wherein the soft portion is formed of a radiopaque material.

14. A catheter as claimed in claim 1 further comprising a guide wire extending through a lumen in the catheter.

15. A catheter as claimed in claim 14, wherein a filter is disposed on the guide wire.

16. A catheter as claimed in claim 15 wherein the catheter is slidable over the guide wire to retrieve the filter.

17. A catheter as claimed in claim 16 wherein the tip expands radially to accommodate the filter.

18. A catheter as claimed in claim 1 wherein the axial reinforcement legs enhance strength in the axial direction.

* * * * *